United States Patent
Höglund et al.

(10) Patent No.: US 12,109,321 B2
(45) Date of Patent: Oct. 8, 2024

(54) SYSTEM AND METHOD FOR REDUCING MICROORGANISMS

(71) Applicant: LED Tailor Oy, Halikko (FI)

(72) Inventors: Camilla Höglund, Halikko (FI); Niko Huhtinen, Halikko (FI)

(73) Assignee: LED Tailor Oy, Halikko (FI)

( * ) Notice: Subject to any disclaimer, the term of this patent is extended or adjusted under 35 U.S.C. 154(b) by 595 days.

(21) Appl. No.: 17/271,984

(22) PCT Filed: Aug. 27, 2019

(86) PCT No.: PCT/FI2019/050607
§ 371 (c)(1),
(2) Date: Feb. 26, 2021

(87) PCT Pub. No.: WO2020/043944
PCT Pub. Date: Mar. 5, 2020

(65) Prior Publication Data
US 2022/0125966 A1    Apr. 28, 2022

(30) Foreign Application Priority Data
Aug. 27, 2018 (EP) ..................................... 18190952

(51) Int. Cl.
   *A61L 2/08*           (2006.01)
   *A61L 2/24*           (2006.01)
   *G01J 1/42*           (2006.01)

(52) U.S. Cl.
CPC .................. *A61L 2/084* (2013.01); *A61L 2/24* (2013.01); *G01J 1/42* (2013.01); *A61L 2202/14* (2013.01); *A61L 2202/25* (2013.01)

(58) Field of Classification Search
CPC ........ A61L 2/084; A61L 2/24; A61L 2202/25; G01J 1/42; A61N 2005/0626; A61N 2005/0663; A61N 5/0624
(Continued)

(56) References Cited

U.S. PATENT DOCUMENTS

2008/0051736 A1    2/2008    Rioux et al.
2008/0059070 A1*   3/2008    Boyden ................ A61B 5/0071
                                            250/492.1
(Continued)

FOREIGN PATENT DOCUMENTS

CN            1287496        3/2001
CN       105 498 096        4/2016
(Continued)

OTHER PUBLICATIONS

Office Action issued on Aug. 25, 2022 in corresponding Chinese Application No. 2019800709127 (with translation), 16 pages.
(Continued)

*Primary Examiner* — Jason L McCormack
(74) *Attorney, Agent, or Firm* — Nixon & Vanderhye PC (57) ABSTRACT

Disclosed is a system and method for reducing microorganisms. The system comprises a light assembly and a processor. The light assembly operable to emit at least two of three different blue lights at different peak wavelengths with a full width half maximum of at most 25 nm, each peak having a time averaged intensity. The peak wavelengths are selected from 400-410 nm, 440-464 nm and 465-490 nm. The processor is communicably coupled to the light assembly to control the time averaged intensities of the blue lights emitted by the light assembly such that if two blue lights are used, the time averaged intensity of one blue light is between 0.67 and 1.33 times the time averaged intensity of another blue light; and if three blue lights are used, the time averaged intensity of any one blue light is between 0.76 and 1.24 times the time averaged intensity of the time averaged intensity of both the other blue lights.

12 Claims, 5 Drawing Sheets

(58) Field of Classification Search
USPC ........................................ 250/453.11, 455.11
See application file for complete search history.

(56) References Cited

U.S. PATENT DOCUMENTS

| | | | |
|---|---|---|---|
| 2016/0030609 A1* | 2/2016 | Peterson | ............ A61L 2/084 362/231 |
| 2016/0030610 A1 | 2/2016 | Peterson et al. | |
| 2017/0014538 A1* | 1/2017 | Rantala | .............. H01L 25/0753 |
| 2017/0080117 A1* | 3/2017 | Gordon | .................. A61L 2/084 |
| 2018/0185529 A1 | 7/2018 | Shur et al. | |
| 2018/0207302 A1 | 7/2018 | Vasilenko | |
| 2018/0243458 A1* | 8/2018 | Shatalov | ................ A61L 9/20 |

FOREIGN PATENT DOCUMENTS

| | | |
|---|---|---|
| CN | 106237350 | 12/2016 |
| CN | 106794357 | 5/2017 |
| CN | 108025182 | 5/2018 |
| DE | 10 2016 110 546 | 12/2016 |
| DE | 102016009175 | 2/2017 |
| KR | 10-1599951 | 3/2016 |
| TW | 201611849 | 4/2016 |
| WO | 2010/004500 | 1/2010 |
| WO | 2017/009534 | 1/2017 |

OTHER PUBLICATIONS

International Search Report for PCT/FI2019/050607 mailed Jan. 16, 2020, 5 pages.
Written Opinion of the ISA for PCT/FI2019/050607 mailed Jan. 16, 2020, 7 pages.
International Preliminary Report on Patentability for PCT/FI2019/050607 mailed Nov. 18, 2020, 9 pages.
Extended European Search Report issued on Feb. 15, 2019 in corresponding European Application No. 18190952.4, 7 pages.
Hessling et al., "Photoinactivation of bacteria by endogenous photosensitizers and exposure to visible light of different wavelengths—a review on existing data," FEMS Microbiology Letters, 364, 2017, fnw270, Dec. 3, 2016, pp. 1-12.
Tomb et al., "Review of the Comparative Susceptibility of Microbial Species to Photoinactivation Using 380-480 nm Violet-Blue Light," Photochemistry and Photobiology, 2018, 94: pp. 445-458.

* cited by examiner

SYSTEM AND METHOD FOR REDUCING MICROORGANISMS

CROSS RELATED APPLICATIONS

This application is the U.S. national phase of International Application No. PCT/FI2019/050607 filed Aug. 27, 2019 which designated the U.S. and claims priority to EP Application No. 18190952.4 filed Aug. 27, 2018, the entire contents of each of which are hereby incorporated by reference.

TECHNICAL FIELD

The present disclosure relates generally to reducing of microorganisms; and more specifically, to systems and methods for reducing microorganisms using blue light at two or more different wavelengths.

BACKGROUND

Microorganisms, such as bacteria, fungi and viruses are omnipresent and constitute a significant bulk of the entire biosphere. A large portion of these microorganisms are pathogens that are responsible for numerous infections and diseases, some of which can be very dangerous and potentially fatal. These pathogens can come in contact with humans through contaminated surfaces, contaminated food, objects, furniture, textiles (i.e. fomites) or through air (as aerosol). According to European Centre for Disease Prevention and Control (ECDC), 6% (country range 2.3%-10.8%) of all European patients are infected with at least one HAI (Health-care associated infection) during their hospital stay. The total annual number of patients with a HAI in European acute care hospitals in 2011-2012 was estimated at 3.2 million. Therefore, upholding and sustaining a certain level of disinfection in public areas and spaces is essential in disease management and prevention, thus maintaining a safe and healthy environment.

The contamination problem is not limited to hospital environments, as contamination via surfaces, objects, air and so forth can also transfer pathogens to foods and food handling equipment, as well as laboratory equipment. Therefore, places such as industrial cleanrooms, food processing facilities, offices, schools, and laboratories among others need appropriate amount of hygiene and controlled environment for prevention of infectious diseases.

By sterilization it is typically meant a process that destroys or eliminates all forms of microbial life and is carried out in health-care facilities by physical or chemical methods. By disinfection, it is typically meant a process that eliminates many or all pathogenic microorganisms, except bacterial spores, on inanimate objects.

Conventional methods for reducing microorganisms or eliminating microorganisms in an indoor environment include, but do not limit to, thermal sterilization (namely, using auto-claves, dry heat and the like), chemical treatment (using metal ions (such as copper/silver ionization), ozone, hydrogen peroxide vapours, germicides (for example antibiotics and biocides), chlorine and compounds thereof and the like), electrochemical disinfection, photoinactivation of the microorganisms using ultraviolet (UV) light, and so forth. Specifically, the photoinactivation of microorganisms has garnered a lot of attention globally for control of growth of microorganisms in the environment. Specifically, the recently developed photoinactivation of the microorganisms achieved by using HINS (High Intensity Narrow Spectrum) technology, narrow-spectrum UV light technology and so forth. However, current photoinactivation techniques target only one of the mechanisms of inactivation in microorganisms. Moreover, UV light is harmful to humans and materials and therefore its use should preferably be avoided.

Photoinactivation of microorganisms with narrowband blue light is of specific interest due to available Light Emitting Diode (LED) technology, providing cost- and energy efficient means for generating such light. For example, photoreactive porphyrins absorb blue light at a peak wavelength of 405 nanometre (nm) to produce reactive oxygen species (ROS). However, different microorganisms have different amounts of photoreactive substances, such as porphyrins and/or flavins, and thus react in an individual manner to different wavelengths of light.

Therefore, the current solutions are not effectively utilizing the full antimicrobial potential of the blue light. Specifically, they fail to target all the crucial and important mechanisms of inactivation of microorganisms that trigger a biological response when activated by the blue light. Furthermore, broad-spectrum light sources are not well adapted for reducing and/or eliminating microorganisms since they waste a lot of energy on wavelengths that have no antimicrobial potential. Furthermore, the UV light technology employs a broad UV light spectrum (ranging from 100 to 400 nanometres) that is damaging materials and harmful for other organisms, such as human and animals. Moreover, some microorganisms have developed resistance to UV light, thereby making the conventional mechanisms ineffective.

Figure 1A:
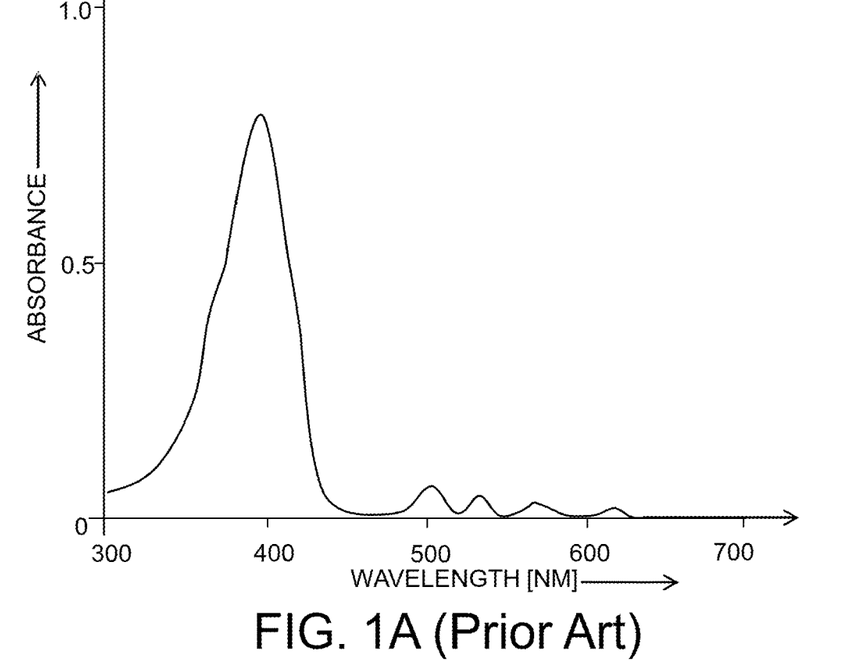
FIG. 1A (Prior Art) is an example graphical representation of absorption spectrum for a porphyrin as a function of wavelength of a light.

FIG. 1A (Prior Art) is an example graphical representation of absorption spectrum for porphyrins as a function of wavelength of a light. As shown, X-axis depicts the wavelength of the light and Y-axis depicts absorbance of the light by the porphyrins. As depicted, the absorption maximum for porphyrins is around 405 nm, i.e. in the range of blue light. Furthermore, as the wavelength of the blue light is increased from 405 nm to 425 nm, there is a steep decrease in the absorbance of the light by the porphyrins.

Figure 1B:
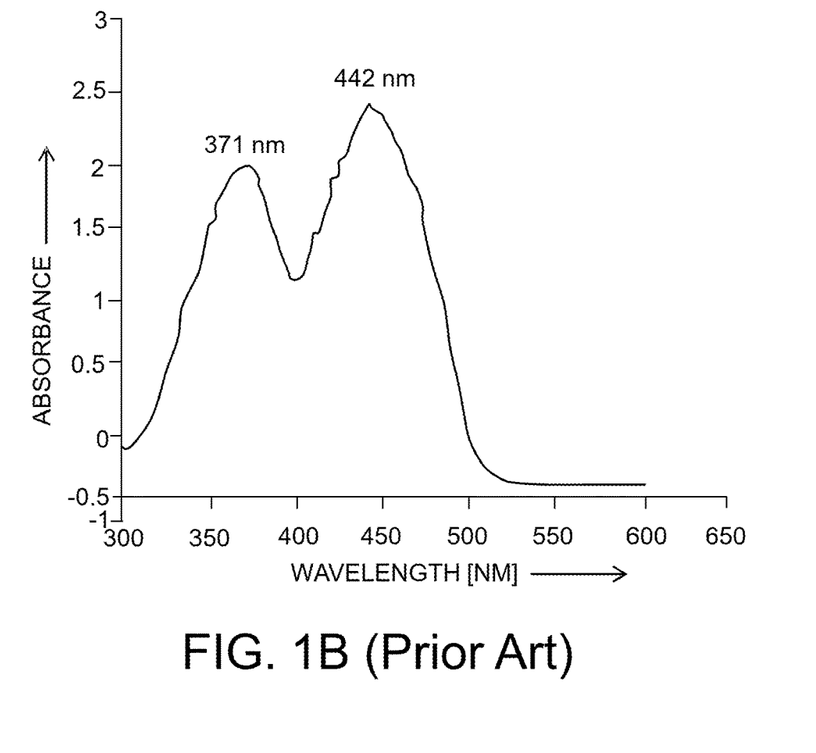
FIG. 1B (Prior Art) is an example graphical representation of absorption spectrum for a flavin as a function of wavelength of a light.

FIG. 1B (Prior Art) is an example graphical representation of absorption spectrum for flavins as a function of wavelength of light. As shown, X-axis depicts the wavelength of the light and Y-axis depicts absorbance of the light by flavins. As depicted, flavins have one absorption maximum in the UV-region, but as UV light is harmful for humans and materials, only the absorption maximum in the blue light region (around 442 nm) is targeted in this invention.

Therefore, in light of the foregoing discussion, there exists a need to overcome the aforementioned drawbacks associated with disinfecting materials, objects and air by targeting more than one photoreactive component of the microorganism simultaneously.

SUMMARY

The present disclosure seeks to provide a system for reducing microorganisms. The present disclosure also seeks to provide a method for reducing microorganisms using the aforementioned system. The present disclosure seeks to provide a solution to the existing problem of reducing growth of microorganisms, for reducing the amount of number of microorganisms and for eliminating microorganisms. An aim of the present disclosure is to provide a solution that overcomes and improves at least partially the problems encountered in prior art and provides an effective and efficient system and method for reducing microorganisms. Indeed, in the present description, "reducing microorganisms" means reducing or lowering the number or amount of microorganisms, most beneficially eliminating all microorganisms. The term "deactivating pathogens" is also sometimes used in this connection. The disclosure seeks to provide a solution for disinfecting surfaces and objects and air within a room, such as a meeting room, a operating room, a bathroom or a cattle shed, wherein the disinfecting effect is sufficient and is produced with relatively small amount of electrical energy. The surfaces include the roof, walls and floor of any room and any objects therein, such as chairs, tables, toilet seats, mats, computers, cell phones, instruments and so forth.

In one aspect, an embodiment of the present disclosure provides a system for reducing microorganisms, the system comprising:

a light assembly operable to emit at least two of:
  a first blue light at a first peak wavelength of 400-410 nm with a full width half maximum of at most 25 nm, the first peak having a first time averaged intensity $I_1$, to target a first photoreactive component of the microorganisms;
  a second blue light at a second peak wavelength of 440-464 nm with a full width half maximum of at most 25 nm, the second peak having a second time averaged intensity $I_2$, to target a second photoreactive component of the microorganisms;
  a third blue light at a third peak wavelength of 465-490 nm with a full width half maximum of at most 25 nm, the third peak having a third time averaged intensity $I_3$, to target a third photoreactive component of the microorganisms; and
a processor communicably coupled to the light assembly to control the time averaged intensities of the blue lights emitted by the light assembly such that if two blue lights are used, the time averaged intensity of one blue light is between 0.67 and 1.33 times the time averaged intensity of another blue light; and if three blue lights are used, the time averaged intensity of any one blue light is between 0.76 and 1.24 times the time averaged intensity of the time averaged intensity of both the other blue lights.

In another aspect, an embodiment of the present disclosure provides a method for reducing microorganisms, via a system comprising a light assembly and a processor, the method comprising:

emitting at least two of
  a first blue light at a first peak wavelength of 400-410 nm with a full width half maximum of at most 25 nm, the first peak having a first time averaged intensity $I_1$, to target a first photoreactive component of the microorganisms;
  a second blue light at a second peak wavelength of 440-464 nm with a full width half maximum of at most 25 nm, the second peak having a second time averaged intensity $I_2$, to target a second photoreactive component of the microorganisms;
  a third blue light at a third peak wavelength of 465-490 nm with a full width half maximum of at most 25 nm, the third peak having a third time averaged intensity $I_3$, to target a third photoreactive component of the microorganisms; and
controlling the time averaged intensities of the blue lights emitted by the light assembly such that if two blue lights are used, the time averaged intensity of one blue light is between 0.67 and 1.33 times the time averaged intensity of another blue light; and if three blue lights are used, the time averaged intensity of any one blue light is between 0.76 and 1.24 times the time averaged intensity of the time averaged intensity of both the other blue lights.

Embodiments of the present disclosure substantially eliminate or at least partially address the aforementioned problems in the prior art for reducing growth of microorganisms using conventional systems and methods of a single-wavelength blue light and enable reducing microorganisms using specific wavelengths of blue light for targeting more than one mechanism of inactivation of the microorganisms.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a system for reducing microorganisms, the system comprising:
  a light assembly operable to emit at least two of:
    a first blue light at a first peak wavelength of 400-410 nm with a full width half maximum of at most 25 nm, the first peak having a first time averaged intensity $I_1$, to target a first photoreactive component of the microorganisms;
    a second blue light at a second peak wavelength of 440-464 nm with a full width half maximum of at most 25 nm, the second peak having a second time averaged intensity $I_2$, to target a second photoreactive component of the microorganisms;
    a third blue light at a third peak wavelength of 465-490 nm with a full width half maximum of at most 25 nm, the third peak having a third time averaged intensity $I_3$, to target a third photoreactive component of the microorganisms; and
  a processor communicably coupled to the light assembly to control the time averaged intensities of the blue lights emitted by the light assembly such that if two blue lights are used, the time averaged intensity of one blue light is between 0.67 and 1.33 times the time averaged intensity of another blue light; and if three blue lights are used, the time averaged intensity of any one blue light is between 0.76 and 1.24 times the time averaged intensity of the time averaged intensity of both the other blue lights.

In another aspect, an embodiment of the present disclosure provides a method for reducing microorganisms, via a system comprising a light assembly and a processor, the method comprising:
  emitting at least two of
    a first blue light at a first peak wavelength of 400-410 nm with a full width half maximum of at most 25 nm, the first peak having a first time averaged intensity $I_1$, to target a first photoreactive component of the microorganisms;
    a second blue light at a second peak wavelength of 440-464 nm with a full width half maximum of at most 25 nm, the second peak having a second time averaged intensity $I_2$, to target a second photoreactive component of the microorganisms;
    a third blue light at a third peak wavelength of 465-490 nm with a full width half maximum of at most 25 nm, the third peak having a third time averaged intensity $I_3$, to target a third photoreactive component of the microorganisms; and
  controlling the time averaged intensities of the blue lights emitted by the light assembly such that if two blue lights are used, the time averaged intensity of one blue light is between 0.67 and 1.33 times the time averaged intensity of another blue light; and if three blue lights are used, the time averaged intensity of any one blue light is between 0.76 and 1.24 times the time averaged intensity of the time averaged intensity of both the other blue lights.

The present disclosure provides the aforementioned system and method for reducing microorganisms. Beneficially, aforementioned system employs dual-wavelength blue light to target more than one mechanism of inactivation of microorganism simultaneously, for reducing microorganisms in a more efficient and faster manner. In one embodiment, the system employs three different peak wavelengths. Specifically, in one embodiment blue lights are employed to activate two or more photoreactive components, such as porphyrins and flavins, of the microorganism to absorb well the blue light at a wavelength of around 405 nm and 450 nm, to release cytotoxic compounds, such as reactive oxygen species (ROS), that kills the microorganisms. The inventors have also observed in recent studies shown that some microorganisms are photoinactivated with wavelengths of 464-490 nm. The underlying mechanism is currently being studied.

In the following, even if a singular is used for the term porphyrin and/or flavin, it is to be understood that the different variants are meant, as typically microorganisms produce various kinds of porphyrins and/or flavins. Moreover, the absorption spectra for different porphyrins and/or flavins does not significantly vary from one another. Furthermore, as is illustrated in FIG. 1B, flavins have one absorption maximum in the UV-region, but as UV light is harmful for humans and materials, only the absorption maximum in the blue light region is targeted in this invention.

Figure 6:
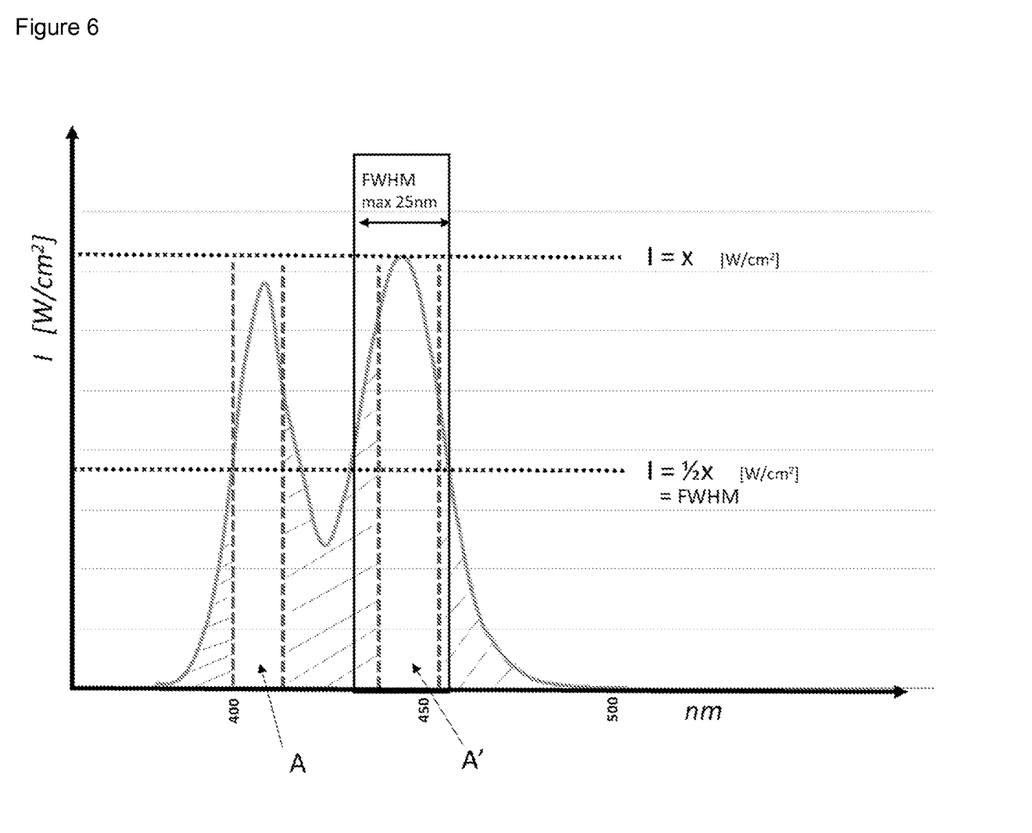
FIG. 6 is a schematic drawing showing the effective area for disinfection.

Additionally, the use of specific wavelengths of blue light prevents wastage of blue light on wavelengths that are not absorbed by the photoreactive compounds in the microorganism as illustrated in FIG. 6. Thus, the aforementioned system is additionally cost-efficient and requires no or negligible manual intervention. Typically, both or all three blue lights are used at the same time, but they may also be used alternately, or if three blue lights are used, any two of them can be used at the same time and alternately with the third blue light. It is also possible to use more than two blue lights, i.e. to use a third and possibly a fourth blue light with a narrow bandwidth and at a specific peak wavelength. Indeed, the light assembly may be further operable to emit a fourth blue light at a fourth peak wavelength, the fourth peak having a fourth time averaged intensity.

According to an embodiment, the system and method uses the mentioned first and second blue lights, or the first and third blue lights, or the second and third blue lights, or all the three blue lights. In case the blue lights are not all on at the same time, it is possible to choose for example that the first and second blue lights are alternately on, the first and third blue lights are alternately on, the second and third blue lights are alternately on, the first and second blue light at on at the same time while alternating with the third blue light, the second and third blue light at on at the same time while alternating with the first blue light, or the first and third blue light at on at the same time while alternating with the second blue light.

The blue light is produced typically with illuminators using LED technology which may use an excitation wavelength that is converted with a phosphor to target wavelengths. Also, other technologies such as laser diodes, optionally combined with phosphors, may be used the produce the narrowband blue light.

As it has been observed that different microorganisms have different amounts of porphyrins and/or flavins, and their amounts may even vary with time for a given microorganism. Using only one blue peak wavelength is not efficient and will not affect the whole range of microorganisms. It has indeed been shown (below in the Experimental part) that the antimicrobial effect of using two target wavelengths is better than the antimicrobial effect achieved when using a single wavelength. Furthermore, since some microorganisms can contain less porphyrins than others, current photoinactivation techniques that only target this mechanism in turn require higher intensities and/or longer illumination time to inactivate microbes with lower porphyrin content.

In the above, the full width half maximum is defined as the bandwidth taken from the peak intensity which includes the range to half the total amplitude. The time averaged intensity of the blue light is defined as the average intensity of the blue light over a treatment time, wherein the treatment time is defined as the time when the light dose (energy) reaches a predefined target light dose. In the present description, the time averaged intensity may sometimes be shorted to simply intensity, while time averaged intensity is meant. This applies to the cases where the time averaged intensities of the blue lights are discussed. Term "intensity" in general refers in this description to illumination power per area ($W/cm^2$). Term light dose refers to intensity ($W/cm^2$) times time (seconds) i.e. $Ws/cm^2$. Alternative term for the light dose used in the description is amount of energy at a surface ($J/cm^2$). Time average intensity (I) should be understood as the sum of light intensities over a period of time. Therefore, time average intensity is the same over a specified time period regardless of using a continuous light source or if the light is pulsed.

The time averaged intensities of the blue lights emitted by the light assembly are such that if two blue lights are used, the time averaged intensity of one blue light is between 0.67 and 1.33 times the time averaged intensity of another blue light, preferably so that the ratio of the two time averages intensities is approximately 1:1; and if three blue lights are used, the time averaged intensity of any one blue light is between 0.76 and 1.24 times the time averaged intensity of the time averaged intensity of both the other blue lights, preferably so that the ratio of the two time averages intensities is approximately 1:1:1. Thus, for example $I_1$ is from $0.67 \times I_2$ to $1.33 \times I_2$; $I_2$ is from $0.67 \times I_3$ to $1.33 \times I_3$ or $I_1$ is from $0.67 \times I_3$ to $1.33 \times I_3$. If three blue lights are used, the ratios of the time average intensities should be within range of $I_1$ and $I_3$ are $0.76 \times I_2$ to $1.24 \times I_2$. The ratios listed above are based on studies by the inventors and represent the maximum deviation of the time averaged intensities. Preferably, the ratios are close to 1:1 in the case of two blue lights and 1:1:1 in the case of three blue lights. In another example, $I_1$ may be from $0.90 \times I_2$ to $1.08 \times I_2$; $I_2$ may be from $0.95 \times I_3$ to $1.02 \times I_3$ or $I_1$ may be from $0.92 \times I_3$ to $1.07 \times I_3$.

It will be appreciated that most microorganisms are minute organisms that are typically visible only under a high-resolution microscope. The microorganisms (or microbes) include, but are not limited to, bacteria, viruses, moulds, and yeasts. Generally, the microorganisms are omnipresent and exist in nature in their unicellular (single-celled) form or in a colony of cells and interact with organisms present in their environment. Typically, microorganisms existing in vegetative form or as biofilm (colonies) are distinguished one from another. According to inventor's knowledge, blue light eliminates microorganisms in both forms (vegetative and biofilm) but other disinfection methods in general do not work well on microorganisms inside a biofilm.

It will be appreciated that light is electromagnetic radiation occupying a predefined portion of the overall electromagnetic spectrum. Specifically, light refers to a visible light that occupies a visible light region of the electromagnetic spectrum. The electromagnetic spectrum comprises a continuum of all electromagnetic waves, such as radio waves, microwaves, infrared, visible light, ultraviolet, X-rays and gamma rays, arranged in a decreasing order of wavelength, energy and/or frequency (wherein the energy and frequency are inversely proportional to the corresponding wavelength). Visible light is defined as 400-780 nm by the Radiation and Nuclear Safety Authority in Finland, although some authorities will categorize 380-780 nm as visual light. The human eye cannot generally see wavelengths under 400 nm, therefore visual blue light is generally defined as 400-500 nm.

Specifically, like all other electromagnetic waves, the visible light propagates as waves and the energy particles imparted by visible light is absorbed by photoreactive metabolites within the organism that is exposed to the visible light. More specifically, a specific range of wavelength of the visible light is absorbed by a specific part of the organism. Indeed, microorganisms produce blue light responsive compounds as a part of their natural metabolism. The blue light responsive compounds produced in microorganisms effectively absorb blue light of very specific wavelengths, while other wavelengths exert no antimicrobial effect. This is further shown in the Experimental part below. Studies show that blue light is not harmful to humans.

Furthermore, blue light has antimicrobial (or microbicidal) properties. Specifically, the blue light photodynamically inactivates the cells of microorganisms, such as fungi, bacteria and the like. More specifically, the microorganisms comprise at least two photoreactive components that absorb blue light at two or more specific wavelengths. The term "photoreactive component" relates to parts inside of a microorganism that absorbs light.

The invention relates to a system for reducing microorganisms, wherein the system comprises a light assembly operable to emit at least two of three blue light peaks having different peak wavelength. Each of the three wavelength peaks is defined to have a full width half maximum (FWHM) of at most 25 nm. As shown herein the absorption wavelengths of the photoreactive compounds in the microorganisms are narrow. This is the wavelength area where there is a biological response in the microorganisms. Therefore, with a narrow full width half maximum of at most 25 nm it can be assured that the energy from the light assembly that can be used for reducing microorganisms (the disinfection power) is concentrated at the wavelength where there is a biological response.

Results shown herein confirms that there is a big difference between different wavelengths in the blue area when it comes to the disinfection efficiency of blue light. FIG. 6 shows in a schematic way that all energy (light) that is emitted in an area (nanometers), which is not absorbed by the photoreactive compounds of the microorganism and thus have no disinfectant power will be wasted. Therefore, to achieve high enough disinfection power in an energy-efficient manner, it is crucial to choose the right blue wavelengths and target only these wavelengths and not waste energy on illuminating with wavelengths that do not add to the disinfection power. This can be achieved with the light assembly according to the invention.

The photoreactive components include organic compounds such as porphyrins, flavins and so forth, that effectively absorb blue light at specific wavelengths (such as 405 nm and 450 nm), resulting in production of cytotoxic reactive oxygen species (indicated by 'ROS' hereafter). Optionally, photoinactivation can occur through via any other mechanism that results in reduction and elimination of microorganisms. Generally, the ROS include for example one of a singlet oxygen (or $^1O_2$), a superoxide anion, a free hydroxyl radical or a hydrogen peroxide molecule, that damage and destroy the cell. The photoinactivation of microorganisms via porphyrins (comprising but not limited to coproporphyrin I, coproporphyrin III, protoporphyrin IX (PPIX) and uroporphyrin I, uroporphyrin III and their derivatives) and flavins (comprising but not limited to riboflavin, flavin adenine dinucleotide (FAD), flavin mononucleotide (FMN) and their derivatives) helps in reducing or eliminating such microorganisms from the surroundings. Thus, a high hygiene can be established, and pathogenic microbes eliminated from air and surfaces in any situation where a certain level of disinfection is required. Furthermore, targeting more than one of the photoreactive components of the microorganisms with specific wavelengths enhances the antimicrobial activity of the blue light.

The system for reducing microorganisms comprises the light assembly operable to emit the chosen at least two blue lights at given peak wavelengths and full width half maximum of at most 25 nm. The various combinations are as discussed above. Specifically, the effectiveness of the blue light in reducing microorganisms is mainly determined by the wavelengths of the blue light and the energy-doses used (which is determined by the time averaged light intensity and illumination time). More specifically, porphyrins have an intense band of absorbance of the blue light with a peak absorbance close to 405 nm, while flavins have an intense band of absorbance of the blue light with a peak absorbance close to 450 nm, and as mentioned above, the mechanism underlying the effect of the third blue light is being studied. Furthermore, specifically, the blue light at peak wavelength of about 450 nm triggers the photoinactivation via flavins (among others FAD/FMN) subsequently initiating the production of ROS. It will be appreciated that the production of ROS induces cleavage of DNA (destroys DNA) in the microorganisms, as well as destroys the microorganism's RNA, protein structure and cell membrane, among others, thereby leading to destruction and deactivation of the microorganism.

The first blue light has a first peak wavelength of 400-410 nm with a full width half maximum of at most 25 nm, i.e. the peak wavelength may be for example from 400, 401, 402, 403, 404, 405, 406, 407, 408 or 409 nm up to 401, 402, 403, 404, 405, 406, 407, 408, 409 or 410 nm. The second blue light has a second peak wavelength of 440-464 nm with a full width half maximum of at most 25 nm, i.e. the peak wavelength may be for example from 440, 441, 442, 443, 444, 445, 446, 447, 448, 449, 450, 451, 452, 453, 454, 455, 456, 457, 458, 459, 460, 461, 462 or 463 nm up to 441, 442, 443, 444, 445, 446, 447, 448, 449, 450, 451, 452, 453, 454, 455, 456, 457, 458, 459, 460, 461, 462, 463, or 464 nm.

The third blue light has a third peak wavelength of 465-490 nm with a full width half maximum of at most 25 nm, i.e. the peak wavelength may be for example from 465, 466, 467, 468, 469, 470, 471, 472, 473, 474, 475, 476, 477, 478, 479, 480, 481, 482, 483 or 484 nm up to 466, 467, 468, 469, 470, 471, 472, 473, 474, 475, 476, 477, 478, 479, 480, 481, 482, 483, 484, 485, 486, 487, 488, 489 or 490 nm.

The full width half maximum of each peak wavelength can be independently for example from 1, 2, 5, 7, 9, 10, 12, 15 or 17 nm up to 5, 7, 9, 10, 12, 15, 17, 18, 20, 23 or 25 nm.

Throughout the present disclosure, the term "light assembly" used herein relates to an arrangement of at least one irradiance means (or light source), arranged in horizontal, vertical or angular position. Optionally, the light assembly comprises a partially closed compartment, having a top section, a bottom section, and at least two walls. Furthermore, the light assembly comprises an attachment means, such as a nail and clip, a vacuum suction cup, a screw, a hook, a bolt and nut combination, a bracket and so on, for attachment for example to a wall or ceiling of a closed cabinet or a room. The light assembly may also comprise two or more irradiance means, one for each wavelength.

In an embodiment, the light assembly comprises at least one of the top sections, the bottom section, walls with at least one slit, at least one bore, a switch, and so forth. Specifically, the at least one slit projects the blue lights emitted by the light assembly at the targeted area of the surrounding. Furthermore, the switch is operable to cause the light assembly to emit the blue lights when in operation or in an ON mode. The at least one bore allows access into the light assembly, such as by a power supply arrangement, operations, and the like. In an example, the light assembly includes a power supply arrangement, arranged via the at least one bore, for supplying power to the light assembly. The power supply arrangement supplies power using conventional methods, including, but not limited to, solar power, electrical energy, chemical energy, rechargeable batteries, fuel-based energy, hydropower and so on. In another example, the light assembly includes a vertical rod, arranged via the at least one bore, for secure placement of the lighting assembly arranged over the vertical rod on the surface or ground. The vertical rod comprises a top edge and a lower section attached to an extended stable platform, such as a tripod stand, a flat-based stand and so on. In yet another example, the light assembly includes a window (or a door) on one of the sections of the partially closed compartment, for the purpose of maintenance of the light assembly.

In an embodiment, the light assembly comprises a light source for irradiating. Specifically, the light source is operable to emit light, namely blue light, at a predefined wavelength. In a preferred embodiment, the light source is a light emitting diode (LED), but it can be any other suitable light source, i.e. a light source capable of emitting light at the required narrow wavelength area and required time averaged intensity, such as a laser diode. The desired wavelengths may be generated using phosphors and an excitation light source. In an embodiment, the light assembly includes a plurality of light sources, preferably LEDs, for example at least two LEDs, electrically coupled with the power supply arrangement arranged within the lighting arrangement.

In one embodiment, the light assembly is operable to emit the first blue light at the first peak wavelength of 400-410 nm with a full width half maximum of at most 25 nm, to target the first photoreactive component of the microorganisms. The range of the first, second and third peak wavelengths are optimally selected for reducing microorganisms. Optionally, the light assembly employs the light source, preferably LED, to emit the first blue light at the first peak wavelength. In an embodiment, more than one LED may be used to emit the first blue light. Furthermore, the first blue light at the first peak wavelength of 400-410 nm with a full width half maximum of at most 25 nm, is targeted at the first photoreactive component of the microorganisms, wherein the first photoreactive component is for example a porphyrin. Indeed, the porphyrin molecule absorbs the first blue light at the wavelength of 400-410 nm well.

According to an embodiment, the light assembly is further operable to emit the second blue light at the second peak wavelength of 440-464 nm with a full width half maximum of at most 25 nm, to target the second photoreactive component of the microorganisms. The range of the second peak wavelength is optimally selected for reducing microorganisms, albeit via a different mechanism than the first peak wavelength. Optionally, the light assembly employs the light source, preferably LED, to emit the second blue light at the second peak wavelength. In an embodiment, more than one LED may be used to emit the second blue light. Furthermore, the second blue light at the second peak wavelength of 440-464 nm with a full width half maximum of at most 25 nm, is targeted at the second photoreactive component of the microorganisms, wherein the second photoreactive component is for example a flavin. Indeed, the flavin molecule absorbs the second blue light at the wavelength of 440-464 nm well.

According to another embodiment, the light assembly is further operable to emit the third blue light at the third peak wavelength of 465-490 nm with a full width half maximum of at most 25 nm, to target the third photoreactive component of the microorganisms. The range of the third peak wavelength is optimally selected for reducing microorganisms, albeit via a different mechanism than the first and/or second peak wavelength. Optionally, the light assembly employs the light source, preferably LED, to emit the third blue light at the third peak wavelength. In an embodiment, more than one LED may be used to emit the third blue light. Furthermore, the third blue light at the third peak wavelength of 465-490 nm with a full width half maximum of at most 25 nm, is targeted at the third photoreactive component of the microorganisms.

The system for reducing microorganisms comprises the processor communicably coupled to the light assembly to control the time averaged intensities of the blue lights emitted by the light assembly. Optionally, the processor regulates the system, by increasing or decreasing the time averaged intensity of the blue lights emitted by the light assembly to reduce microorganisms. Specifically, the time averaged intensity of blue light is measured as power and time per unit area of a surface. For example, the time averaged intensity of blue light may be 10 Watt seconds per square centimetre (indicated by 'Ws/cm$^2$' hereafter). The time averaged intensity of the blue light varies with the blue light source. Specifically, different time averaged intensities of blue light have specific applications in different fields.

Optionally, the system further comprises at least one light sensor, communicably coupled to the processor, configured to detect the time averaged intensities of the blue lights emitted by the light assembly, wherein the processor is configured to control the time averaged intensities of the blue lights when the blue light energy at the surface exceeds a predefined threshold limit. The predefined threshold limit can be set for example between 1 and 100 Ws/cm$^2$. Specifically, the at least one light sensor is used to accurately detect the time averaged intensities of the blue lights emitted by the light assembly. More specifically, the at least one light sensor records the detected time averaged intensities of the blue lights emitted by the light assembly as a light sensor data. In case three blue light is used, the light sensor is configured to detect the time averaged intensity of all the blue lights and the processor is configured to control the time averaged intensity of all the blue lights, etc. The light sensor sends the light sensor data, comprising information related to the time averaged intensities of the blue lights emitted by the light assembly, to the processor. The processor is configured to receive the light sensor data from the light sensor and regulate the time averaged intensities of the blue lights when the blue light energy at the surface exceeds a predefined threshold limit. Since the present disclosure relates to targeted photoinactivation of microorganisms, it is essential to reach and maintain optimum levels of blue light energy at the surface to guarantee a sufficient level of disinfection. In case only a short time is available for using the present system and method, it is possible to increase the time averaged intensity of the blue lights to obtain an optimum level of disinfection.

In an embodiment, the blue lights are emitted by the light assembly at a time averaged intensity that provides blue light energy at a surface that exceeds over 1 watt×second per square centimetre (Ws/cm$^2$). Specifically, a blue light energy of more than 1 Ws/cm$^2$ assures that a minimum cytotoxic amount of ROS is produced in the microorganism as result of blue light absorption by the corresponding photoreactive compounds in the microorganism.

For the time being, it is not known that there would be an upper limit to the blue light energy required to activate the photoreactive compounds to produce sufficient reactive oxygen species (ROS) that is highly cytotoxic and kills the microorganism. However, there is a practical limit of continuous output time averaged intensity of the components of the light assembly related to heat production and lifetime. The upper limit is thus typically 100 kWs/cm2 in continuous operation.

On the other hand, it may be noted that blue light energy at 1 Ws/cm$^2$ or below may result in the reverse antimicrobial property of the blue light and enhance the growth of microorganisms (as is shown in the Figures). Also, providing a light source with a broad wavelength such as white light or ambient light or some specific wavelengths might enhance the growth of microorganisms thereby reducing the disinfection property of the light assembly according to the invention. According to an embodiment, if the relative ratio of time averaged intensities is kept at a substantially constant level at the target surface, i.e if intensity of one blue light is altered, the time averaged intensity of another blue light is altered as well. Dose (amount of energy) is preferably controlled by adjusting the time said light is on with said time averaged intensity. If the dose is controlled by controlling time averaged intensity, the time averaged intensity values of both blue lights (or all blue lights) are controlled.

In an embodiment, the light assembly comprises at least two light sources operable to emit the blue lights at the desired wavelengths, and the processor is operable to control the light source to alternatively emit the blue lights in a periodic manner. Optionally, a single light source, preferably LED, may be used to emit blue light of two (or three) different wavelengths. More optionally, the processor is operable to control the light source to alternatively emit the blue light of two or three different wavelengths. Specifically, the processor operates the LED to emit first one blue light at one wavelength and a second blue light at its given wavelength in a periodic manner. For example, for the first five seconds, only blue light with the first peak wavelength of 400-410 nm, preferably 405 nm, with a full width half maximum of at most 25 nm, is emitted, and thereafter, for the next 5 seconds only the blue light with the second peak wavelength of 440-464 nm, preferably 450 nm, with a full width half maximum of at most 25 nm, is emitted. The same combinations as discussed above apply also here, while the times may be any suitable times.

In another embodiment, the light assembly comprises two light sources each operable to emit a given blue light. The light assembly may also comprise three light sources, each operable to emit a given blue light. In yet another embodiment, the light assembly may comprise two light sources, one being operable to emit two different blue lights and the other to emit the third blue light. The processor is operable to control the first and second light sources to simultaneously emit the blue lights. Optionally, two distinct light sources, preferably two LEDs, may be used to emit blue light of two different wavelengths, such that each of the light sources emit either one blue light or another blue light. More optionally, the processor is operable to control each of the two light sources to simultaneously emit the blue lights. Specifically, for example, the processor operates the first LED light source to emit the first blue light at the first wavelength and the second LED light source to emit the second blue light at the second wavelength simultaneously or alternately. For example, the first LED light source may emit blue light with the first wavelength of 400-410 nm, preferably 405 nm, with a full width half maximum of at most 25 nm, for the first five seconds, and at the same time the second LED light source may emit blue light with the second wavelength of 440-464 nm, preferably 450 nm, with a full width half maximum of at most 25 nm.

Optionally, the processor is operable to control the light source(s) to emit blue lights simultaneously in one of the ways: continuously, in short pulses (bursts) or in long pulses. Specifically, the first light source and the second light source may emit respective blue lights of specific wavelengths continuously to reduce microorganisms.

Optionally, the system further comprises at least one sensor, communicably coupled to the processor, wherein the at least one sensor is operable to detect the presence or movement of an object within a target area subjected to the blue lights emitted by the light assembly, and wherein the at least one sensor is operable to instruct the processor to control the time averaged intensities of the blue lights in the target area. The moving object may be a person or an animal. Optionally, the at least one sensor includes, but is not limited to, a motion sensor, an infrared sensor, an imaging device and so on. Specifically, the motion sensor is a kind of an infrared sensor that detects the proximity of the moving object, such as human or the animal within the target area subjected to the blue lights emitted by the light assembly. More specifically, the motion sensor may for example detect a change in infrared thermal heat patterns in the area in the vicinity of the motion sensor. Furthermore, the motion sensor may use a pair of pyroelectric elements for sensing the change in temperature due to infrared thermal heat patterns. Consequently, instantaneous differences in an output generated at the two pyroelectric elements are detected as movements, specifically of the heat-radiating objects, such as humans or animals.

In an embodiment, the at least one sensor is operable to instruct the processor to control the time averaged intensities of the blue lights in the target area. Specifically, the at least one sensor is used to accurately detect the presence or movement of an object within the target area subjected to the blue lights emitted by the light assembly. More specifically, the at least one sensor records the information about the moving object as a sensor data. The at least one sensor sends the sensor data, comprising information related to the presence of the moving object within the target area subjected to the blue lights emitted by the light assembly, to the processor. The processor is configured to receive the sensor data from the at least one sensor and control the time averaged intensities of the blue lights in the target area based on the received sensor data.

Optionally, the processor is operable to control the time averaged intensities of the blue lights simultaneously in one of the ways: continuously, in short pulses (bursts) or in long pulses. Specifically, the time averaged intensities of the lights may be controlled to emit the respective blue lights continuously to reduce microorganisms.

Optionally, the first light source and the second light source may emit respective blue lights of specific wavelengths in short or long pulses to reduce microorganisms. Specifically, the blue lights are emitted in short or long pulses if the at least one sensor detects the presence of a moving object such as human or animal. More specifically, the processor is operable to reduce the time averaged intensities of the blue lights in the presence of a moving object, at certain point on time, within the target area subjected to the blue lights emitted by the light assembly.

Optionally, instructing the processor based on detection of the presence or movement of an object comprises switching the light assembly between a disinfecting mode and an ambient mode. Specifically, the processor receives the sensor data, comprising information about detection of the presence or movement of an object, from the at least one sensor. More specifically, based on the instructions received from the sensor data, the processor operates the light assembly to switch between the disinfecting mode and the ambient mode. The term "disinfecting mode" refers to a state of operation of the light assembly in a manner that the reduction of the microorganism is maximum. Specifically, the first and second light sources may be switched ON to radiate the blue lights to reduce microorganisms. The system may also be configured to be continuously in the disinfecting mode, or it may be manually set to disinfecting mode when desired. Alternatively, the system may be equipped with a predefined disinfecting program (including times to have the system ON and times to have it OFF).

Optionally, when the light assembly is arranged to be operated in the disinfecting mode, the processor is configured to control the light assembly to emit the blue lights at a time averaged intensity that provides over 1 Ws/cm$^2$ blue light energy at the surface for reducing microorganisms. Specifically, when the presence or movement of an object is not detected by the at least one sensor, the light sources operate normally, by continuously radiating the blue light of corresponding wavelengths to reduce microorganisms. In an embodiment, the processor may increase the time averaged intensities of the blue lights to reduce microorganisms based on the sensor data generated by the at least one sensor, i.e. when the presence of a moving object is not detected by at least one sensor. It may however be noted that the light-dose below a threshold value, in this case 1 Ws/cm$^2$, may have stimulatory effect on the growth of microorganism, even while under the effect of the first and second blue lights. Light sources of other wavelengths than the first and second blue light or broad wavelength light such as white light may also have a stimulatory effect on the growth of microorganisms and should thus be avoided for optimal disinfection.

It will be appreciated that an optimal threshold of time averaged intensity of light that delivers light-dose or blue light energy and the wavelength of the blue light is essential for the antimicrobial activity of the blue light. Additionally, the present disclosure utilizes dual-wavelength (or two/three effective wavelengths). Beneficially, the dual-wavelength (for example 405 nm+450 nm) blue LED technology is more efficient in reducing microorganisms than using just one blue wavelength of for example 405 nm. This is illustrated in the Experimental section below.

It will be appreciated that there are variations within species of microorganisms. Such variations result in difference in their response to the blue light. Specifically, the difference in the response to the blue light is due to the variations in metabolites or the photoreactive compounds of the microorganisms that respond to the blue light. In an example, if one microorganism contains less porphyrin than others, and similarly if another microorganism contains less flavin than others, their susceptibility to be reduced by the blue light is highly varied from other microorganisms with higher levels of porphyrin and/or flavin in them. Beneficially, the present disclosure provides, according to one embodiment, a technology that targets all the biologically relevant metabolites using the dual-wavelength (405 nm+450 nm) blue light to target the photoreactive compounds or metabolites of the microorganisms, thus inactivating them irrespective of their individual variations.

The term "ambient mode" refers to a stage when the time averaged intensities of the light source(s) is/are adjusted such that the blue light energy imparted at the surface of the target area is not visually impractical or unpleasant. Optionally, the ambient mode is characterized by the emitted light having a light temperature in a range from 3000-10000 K.

The system may be configured to automatically switch off the blue light source(s) when a presence or movement is detected within a space. Alternatively, the system may be configured to lower the time averaged intensity of the blue lights when presence or movement is detected.

Optionally, in such instance, the light assembly further comprises a light source operable to emit white light at a certain wavelength in the ambient mode based on the data of the at least one sensor. Specifically, the white light source may be a LED. More specifically, the white light source may be operable to emit the white light only when the light assembly is arranged to be operated in the ambient mode, based on detection of presence or movement of an object within the target area. Furthermore, the processor may be configured to control the time averaged intensities of the blue lights and the white light based on the detection of the presence or movement of an object by the at least one sensor. More specifically, in the presence or movement of an object, the processor may be configured to lower the time averaged intensities of the blue lights to make the light appear white. Beneficially, the decrease in the time averaged intensities of the blue lights prevents the presence or moving object to be exposed to the potentially unpleasant blue light.

In an embodiment, the processor is configured to gradually increase the time averaged intensities of the blue lights and decrease the time averaged intensity of white light to maintain the overall time averaged intensity of light, based on the sensor data, specifically, when the presence of a moving object has ceased to exist within the target area. For example, the processor may gradually increase the time averaged intensities of the blue lights each by 10-50 percent per minute and decrease the time averaged intensity of white light by 10-50 percent per minute.

Optionally, the system further comprises a microbe sensing module, communicably coupled to the processor, configured to detect the presence of microorganisms, wherein the processor is configured to control the time averaged intensities of the blue lights emitted by the light assembly based on the detection of the presence of microorganisms. Specifically, the microbe sensing module may comprise at least one of a fluorescent detector, an infrared sensor, an imaging device, and the like. More specifically, the microbe sensing module effectively detects the presence of microorganisms within the target area subjected to the blue lights emitted by the light assembly. Furthermore, the microbe sensing module may detect a change in the infrared thermal heat patterns at a microscopic level in the area in the vicinity of the microbe sensing module.

In an embodiment, the microbe sensing module is operatively coupled to the processor. Specifically, the microbe sensing module is used to accurately detect the presence of microorganisms within the target area. More specifically, the microbe sensing module records the information about the presence of microorganisms as a microbe sensing data. The microbe sensing module sends the microbe sensing data, comprising information related to the presence of microorganisms within the target area, to the processor. The processor is configured to receive the microbe sensing data from the microbe sensing module and control the time averaged intensities of the blue lights emitted by the light assembly based on the detection of the presence of microorganisms.

Furthermore, the processor is operable to control the time averaged intensities of the blue lights emitted by the light assembly based on the detection of the presence of microorganisms. In an embodiment, the processor is configured to gradually increase the time averaged intensities of the blue lights in the presence of microorganisms within the target area. For example, the processor may gradually increase the time averaged intensities of the blue lights each by 1 percent per minute to maintain the overall time averaged intensity of light thus providing over 1 Ws/cm2 energy on the surface or a cross-section of air. It is however assumed that a fast increase (i.e. practically immediate increase) is better in practice.

In this context, by a cross-section of air it is meant a cross section of air that is to be disinfected. This means that the present system also works on air, not only on surfaces. It should be understood that primarily the solution is intended and dimensioned to disinfect surfaces and objects, however, there is a volume of air in between the surface and the light assembly. As the blue light penetrates air, the air bound microbes also absorb the blue light. Furthermore, as blue light time averaged intensity is dimensioned to disinfect the surface, and the volume of air is closer to the light assembly, thus receiving a larger dose of the blue light energy per unit of time.

In an embodiment, the system further comprises at least one optical element arranged with the light assembly, and the at least one optical element is configured to direct the blue lights emitted by the light assembly. The term "optical element" used herein relates to optical components for directing the light to a target area. Typically, the at least one optical element includes, but is not limited to, a lens, an aperture device, a mirror, a prism, a waveguide and the like. Specifically, the at least one optical element is arranged in such a way that the narrow beam of blue light, comprising the chosen blue light(s), emitted by the light assembly is further concentrated upon the target area. More specifically, the concentrated beam of blue light, comprising the chosen blue light(s), emitted by the light assembly may be more efficient in reducing microorganisms on the target area subjected to the blue light emitted by the light assembly. The system may also comprise an optical element for each light source, or it may comprise one optical element for all light sources.

Optionally, the system further comprising a clock module communicably coupled to the processor, and the clock module is operable to provide a time plan for adjusting the time averaged intensities of the blue lights emitted by the light assembly to reduce microorganisms. The clock module maybe a hardware, software, firmware or a combination of these, operable to provide a time plan for adjusting the time averaged intensities of the blue lights. In an embodiment, the clock module is arranged with the processor. In another embodiment, the clock module may be arranged at a remote location. In such an embodiment, the clock module is communicably coupled to the processor via a wired network, a wireless network or any combination thereof. Examples of the network between the clock module and the processor include, but are not limited to, Local Area Networks (LANs), Wide Area Networks (WANs), radio network, Internet, radio networks, and telecommunication networks.

Optionally, the term "time plan" used herein refers to the schedule based on which the time averaged intensities of the blue light emitting from the light source(s) are adjusted to reduce microorganisms. It may be appreciated that the time plan is provided based on the light sensor data, at least one sensor data and microbe sensing data. In first example, the time plan may comprise a time period in a day, such as from 10 PM to 6 AM. In such an example, when the light assembly is arranged to be operated in the disinfecting mode, the time plan may be provided from 10 PM to 6 AM when the target area, such as a hospital, a school, an office, a laboratory, a library, or a section thereof, is not accessed by humans. Furthermore, when the target area is being accessed by humans, the clock module may schedule a time plan in such a manner that the light assembly is arranged to be operated in the ambient mode at those times.

Furthermore optionally, the clock module is further operable to measure a time duration when the light assembly is arranged to be operated in the disinfecting mode. As discussed in the first example, when the light assembly is arranged to be operated in the disinfecting mode from 10 PM to 6 AM, the clock module is operable to measure the time duration to be 8 hours (10 PM of Day 1 till 6 AM of Day 2)).

Optionally, the clock module is further operable to determine a time taken to substantially reduce microorganisms to generate a time-data based on the time plan and the measured time duration. The term "time data" used herein relates to the effective time taken to substantially reduce microorganisms. Furthermore, when the target area is being accessed by humans, the clock module may generate a time data based on the detection of the presence of a moving object by the at least one sensor. Optionally, if the target area is being accessed by humans regularly during the same time of the day, the clock module is operable to reset the time plan.

In an embodiment, the system further comprises a server arrangement communicably coupled to the processor, wherein the server arrangement is operable to provide a time plan for adjusting the time averaged intensities of the blue lights emitted by the light assembly to reduce microorganisms. Optionally, the processor is operable to receive the time plan from the server arrangement and control the time averaged intensities of the blue lights emitted by the light assembly based on the time plan.

In another embodiment, the server arrangement is operable to provide a time plan for adjusting the time averaged intensities of the blue lights and the time averaged intensity of the white light emitted by the light assembly to reduce microorganisms. Optionally, the processor is operable to receive the time plan from the server arrangement and control the time averaged intensities of the blue lights and the time averaged intensity of the white light emitted by the light assembly based on the time plan and the sensor data. More optionally, the processor lowers the time averaged intensities of the blue lights and increases the time averaged intensity of the white light if the at least one sensor detects the presence of a moving body in the target area.

In an example, when the light assembly is arranged to operate in the ambient mode, the time plan may comprise a time period in a day at which the time averaged intensities of the blue lights and the intensity of the white light are adjusted to reduce microorganisms and to simultaneously maintain the colour temperature within the desired range.

The server arrangement can be communicably coupled to the processor through a communication network, including but not limited to, Local Area Networks (LANs), Wide Area Networks (WANs), Metropolitan Area Networks (MANs), Wireless LANs (WLANs), Wireless WANs (WWANs), Wireless MANs (WMANs), the Internet, second generation (2G) telecommunication networks, third generation (3G) telecommunication networks, fourth generation (4G) telecommunication networks, fifth generation (5G) telecommunication networks, Worldwide Interoperability for Microwave Access (WiMAX) networks and suchlike.

Optionally, the server arrangement comprises a database, wherein the database is configured to store the time plan. More optionally, the database is configured to receive the preconfigured time plan, corresponding to the disinfecting mode and ambient mode, from the server arrangement.

The present disclosure also relates to the method as described above. Various embodiments and variants disclosed above apply mutatis mutandis to the method.

Optionally, the method comprises detecting a presence of the moving object, using the at least one sensor, to instruct the processor to control the time averaged intensities of the blue lights emitted in the target area, wherein instructing the processor based on detection of the presence of the moving object comprises switching the light assembly between the disinfecting mode and the ambient mode.

Optionally, when the light assembly is arranged to be operated in the disinfecting mode, the method further comprises controlling the light assembly to emit the blue lights at the time averaged intensity that provides over 1 Watt second per square centimetre blue light energy at the surface for reducing microorganisms.

Optionally, the method further comprises providing a time plan for adjusting the time averaged intensities of the blue lights emitted by the light assembly to reduce microorganisms, measuring the time duration when the light assembly is arranged to be operated in the disinfecting mode, and determining the time taken to substantially reduce microorganisms to generate the time-data based on the time plan and the measured time duration.

EXPERIMENTAL SECTION

In an exemplary implementation, a dual-wavelength (405 nm+450 nm) blue LED light is more effective in terms of its antimicrobial activity as compared to single-wavelength (405 nm or 450 nm) blue LED lights in reducing the amount of *Escherichia coli* (*E. coli*).

It may be noted from Table 1 that the dual-wavelength (405 nm+450 nm) blue LED light provided nearly 100% inactivation (2 $\log_{10}$ reduction) at a very low light-dose, i.e. at 10 Ws/cm$^2$ and 3 $\log_{10}$ reduction at 15 Ws/cm$^2$, while neither of the single-wavelength (405 nm or 450 nm) blue LED lights could provide similar results. It will be appreciated that achieving a 2 $\log_{10}$-3 $\log_{10}$ reduction at a very low light-dose (10-15 Ws/cm$^2$) establishes the high efficiency and effectiveness of the dual-wavelength (405 nm and 450 nm) blue LED lights in reducing microorganism as compared to the single-wavelength (405 nm) blue LED light that requires a light-dose of 270 Ws/cm$^2$ to achieve a similar level of reduction.

TABLE 1 wherein AR stands for average reduction, all reductions are percentages

| Energy (light-dose) (Ws/cm$^2$) | Single wavelength; 450 nm | | | Dual wavelength; 405 nm + 450 nm | | | | Single wavelength; 405 nm |
|---|---|---|---|---|---|---|---|---|
| | Case 1 | Case 2 | AR | Case 3 | Case 4 | Case 5 | AR | AR |
| 5 | 78 | 64 | 71 | 89 | 85 | 90 | 88 | — |
| 10 | 79 | 86 | 83 | 100 | 99 | 100 | 99.7 | — |
| 15 | 82 | 84 | 83 | 99.5 | 100 | 100 | 99.9 | — |
| 21 | | | | | | | | 82.3 |
| 58-180 | | | | | | | | 90-97.3 |
| 270 | | | | | | | | 99.8 |

Optionally, the optimal intensity and corresponding wavelengths of the first and second blue lights activates the porphyrin and the flavin compounds to produce ROS that results in reducing microorganisms in the target area subjected to the blue light emitted by the light assembly. In an exemplary implementation, a difference in antimicrobial efficiency between different wavelengths of the blue light is provided in Table 2. Furthermore, a $Log_{10}$) reduction and the reduction of microorganisms (η) for the inactivation of *Staphylococcus aureus* after being exposed to a blue light of wavelength ranging from 400-430 nm at a light-dose of 23.5 Ws/cm$^2$ depicts that the maximum effectiveness of the antimicrobial activity of the blue light is achieved at 405±5 nm (where ±stands to indicate the bandwidth, the same abbreviation being used later below).

TABLE 2

Reduction of *Staphylococcus aureus* as a function of wavelengths with the same energy dose

| Wavelength | Initial Population, $N_0$ ($Log_{10}$CFU mL$^{-1}$) | Final Population, N ($Log_{10}$CFU mL$^{-1}$) | $Log_{10}(N/N_0)$ Reduction | η ($Log_{10}(N/N_0)$/ 23.5 Ws/cm$^2$) |
|---|---|---|---|---|
| 400 ± 5 nm | 5.36 (±0.02) | 3.83 (±0.01) | 1.5 | 0.064 |
| 405 ± 5 nm | 5.29 (±0.01) | 2.89 (±0.07) | 2.4 | 0.102 |
| 410 ± 5 nm | 5.31 (±0.03) | 4.16 (±0.18) | 1.1 | 0.047 |
| 415 ± 5 nm | 5.20 (±0.03) | 4.65 (±0.07) | 0.5 | 0.021 |
| 420 ± 5 nm | 5.26 (±0.01) | 4.99 (±0.01) | 0.3 | 0.013 |
| 430 ± 5 nm | 5.35 (±0.03) | 5.25 (±0.05) | 0.1 | 0.004 |

It may be noted that at a wavelength of 405 nm, the amount of *Staphylococcus aureus* is reduced significantly compared to the other tested wavelengths, thereby establishing that the blue light at a wavelength of 405 nm has the maximum antimicrobial activity.

In another exemplary implementation, importance of the wavelength and the intensity of the blue light required to reduce microorganisms is provided in Table 3. Furthermore, microorganisms *Porphyromonas gingivalis* and Methicillin-resistant *Staphylococcus aureus* (MRSA) require varying light doses to reduce the amount of microorganisms by a level of 1 $log_{10}$ (i.e. more than 90%). It will be appreciated that a small difference in the wavelength of blue light can result in a vast difference of blue light energy required to reduce the number of microorganisms.

As depicted, at a wavelength of 405 nm, the blue light energy required for *Porphyromonas gingivalis* is the lowest, meaning that blue light energy would be needed less if *Porphyromonas gingivalis* was targeted with a wavelength of 405 nm. Furthermore, at a wavelength of 450 nm, the blue light energy required for Methicillin-resistant *Staphylococcus aureus* (MRSA) is the lowest, meaning that the blue light energy would be needed less if MRSA was targeted with a wavelength of 450 nm. Thus, these wavelengths are most efficient in eliminating the above microbes.

TABLE 3

| Microorganism | Wavelength | Light-dose required to reduce 1$log_{10}$ (>90%) microorganisms |
|---|---|---|
| *Porphyromonas gingivalis* | 405 nm | 41 Ws/cm$^2$ |
| | 425 nm | 524 Ws/cm$^2$ |
| | 450 nm | 47 Ws/cm$^2$ |
| | 455 nm | 49 Ws/cm$^2$ |
| | 465 nm | 94 Ws/cm$^2$ |
| Methicillin-resistant *Staphylococcus aureus* (MRSA) | 405 nm | 62 Ws/cm$^2$ |
| | 450 nm | 32 Ws/cm$^2$ |
| | 460 nm | 120 Ws/cm$^2$ |
| | 464 nm | 61 Ws/cm$^2$ |

DETAILED DESCRIPTION OF THE DRAWINGS

Figure 2:
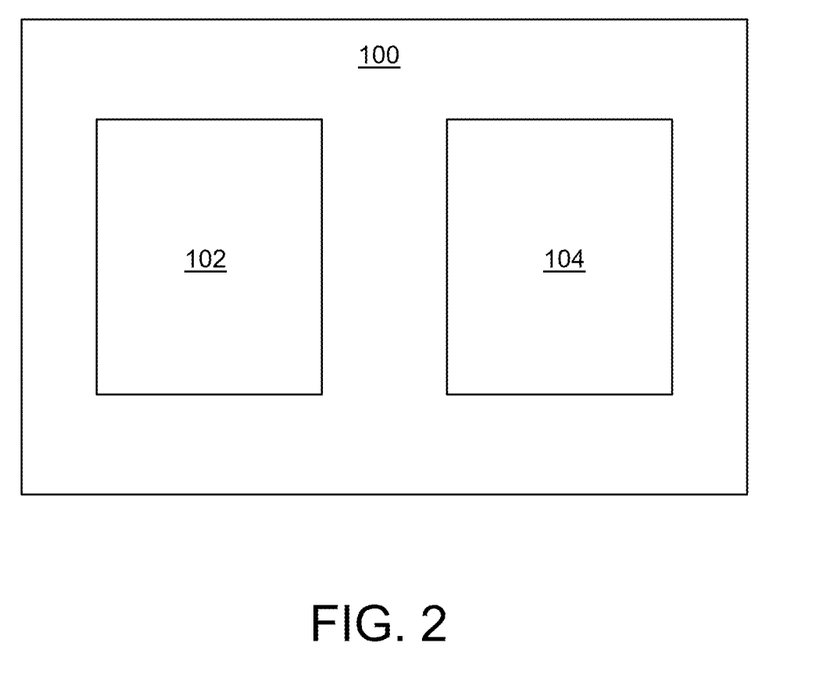
FIG. 2 is a block diagram of a system for reducing microorganisms, in accordance with an embodiment of the present disclosure.

Referring to FIG. 2, illustrated is a block diagram of a system 100 for reducing microorganisms, in accordance with an embodiment of the present disclosure. As shown, the system comprises a light assembly 102 and a processor 104 communicably coupled to the light assembly 102. The light assembly 102 emits a first blue light at a first peak wavelength of 400-410 nm with a full width half maximum of at most 25 nm, to target a first photoreactive component of the microorganisms, and a second blue light at a second peak wavelength of 440-464 nm with a full width half maximum of at most 25 nm to target a second photoreactive component of the microorganisms. Optionally the light assembly 102 comprises emit a third blue light at a second third peak wavelength of 465-490 nm with a full width half maximum of at most 25 nm to target a third photoreactive component of the microorganisms. Optionally the light assembly 102 comprises a fourth white light to provide ambient lighting mode. The processor 104 is configured to control time averaged intensities of the first blue light, the second blue light, and the optional third blue light and fourth white light emitted by the light assembly 102.

Figure 3:
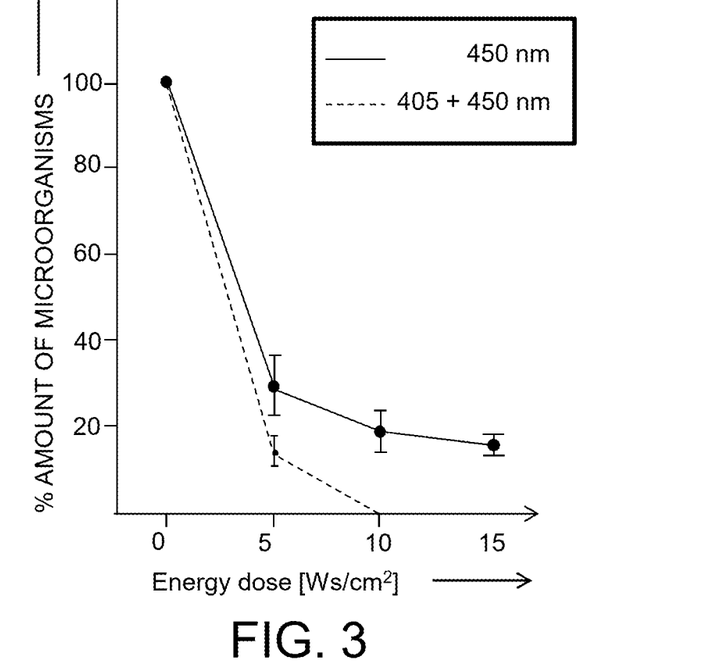
FIG. 3 is a graphical representation of differences between single- and dual blue wavelengths systems, with a relative amount (%) of microorganisms as a function of light energy dose, in accordance with an embodiment of the present disclosure.

Referring to FIG. 3, illustrated is a graphical representation of an relative amount of microorganism as a function of light energy dose, in accordance with an embodiment of the present disclosure. As shown, the X-axis represents the energy dose used for reduction of microorganisms, whilst the Y-axis represents the amount of microorganisms in percentage. The solid line represents amount of microorganism when a blue light with a wavelength 450 nm is used and the dashed line represents the amount of microorganisms when a first blue light and a second blue light with wavelengths 405 and 450 nm respectively, is used (as in Table 1).

As shown, using single wavelength blue light of 450 nm is less effective in reducing microorganisms as compared to using dual wavelength blue light (the first blue light and the second blue light, wavelengths 405 and 450 nm respectively). As depicted, when a surface is exposed to the blue light of wavelength 450 nm so that an energy dose of 5 Ws/cm$^2$ is reached, there is 70% reduction of the microorganisms on the surface compared to control. In comparison, when the surface is exposed to the first and second blue light of wavelength 405 and 450 nm respectively until an total energy dose of 5 Ws/cm$^2$ is reached, there is 90% reduction of the microorganisms on the surface. Moreover, when a surface is exposed to the blue light of wavelength 450 nm until an energy dose of 10 Ws/cm$^2$ is reached, there is 80% reduction of the microorganisms on the surface, whilst when the surface is exposed to the first and second blue light of wavelength 405 and 450 nm respectively until an energy dose of 10 Ws/cm$^2$ is reached, approximately 99% microorganisms present on the surface are killed. At an energy dose of 15 Ws/cm$^2$, the amount of microorganisms has further slightly reduced with the dual blue wavelength system. Therefore, it is to be understood that a dual blue wavelength light (405 nm+450 nm) is more antimicrobial than using a single wavelength blue light.

Figure 4:
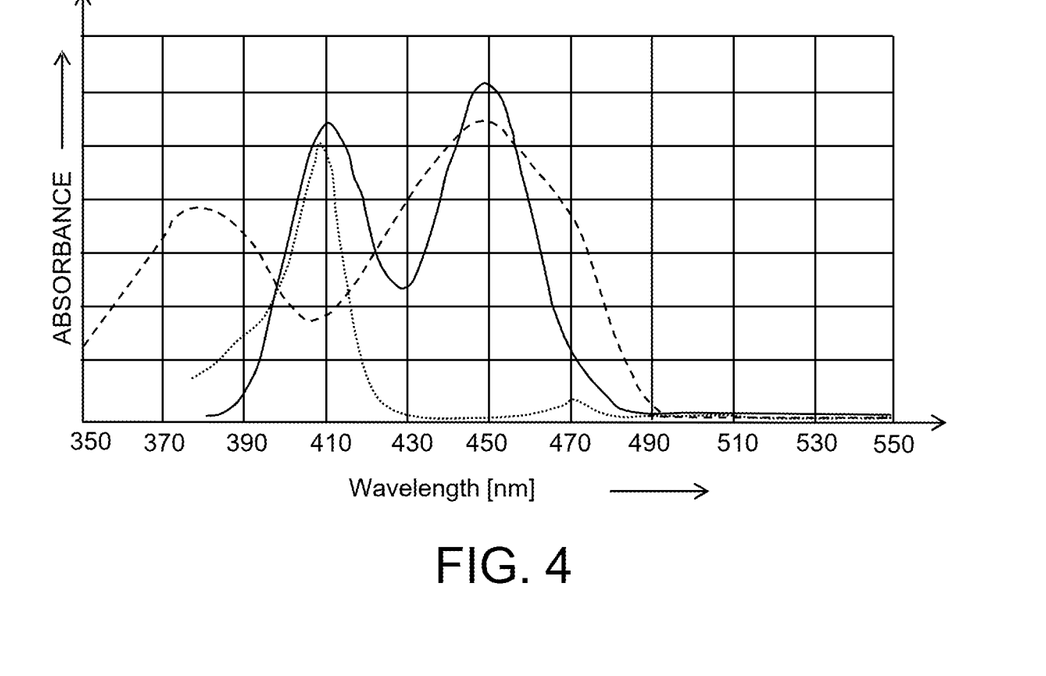
FIG. 4 is an example graphical representation of absorption spectrum for a first photoreactive component (such as a porphyrin) and a second photoreactive component (such as a flavin) as a function of wavelength of a blue light, in accordance with an embodiment of the present disclosure.

Referring to FIG. 4, illustrated is an example graphical representation of absorption spectrum for a first photoreactive component (such as porphyrin) and a second photoreactive component (such as flavin) as a function of wavelength of a blue light, in accordance with an embodiment of the present disclosure. As shown, X-axis depicts the wavelength of the light and Y-axis depicts absorbance of the blue light by the first photoreactive component and the second photoreactive component. The dotted line represents absorption spectrum for the first photoreactive component and the dashed line represents absorption spectrum for the second photoreactive component, whilst the solid line represents emission spectrum associated with the blue light emitted by the light assembly. As shown, the maximum absorbance of blue light by the first photoreactive component and the second photoreactive component is at ca 405 nm and ca 450 nm respectively. Therefore, the first blue light is provided at a first peak wavelength of 400-410 nm with a full width half maximum of at most 25 nm, to target the first photoreactive component of the microorganisms with a maximum absorbance of blue light at ca 405 nm, and a second blue light at a second peak wavelength of 440-464 nm with a full width half maximum of at most 25 nm, to target the second photoreactive component of the microorganisms with a maximum absorbance of blue light at ca 450 nm.

Figure 5A:
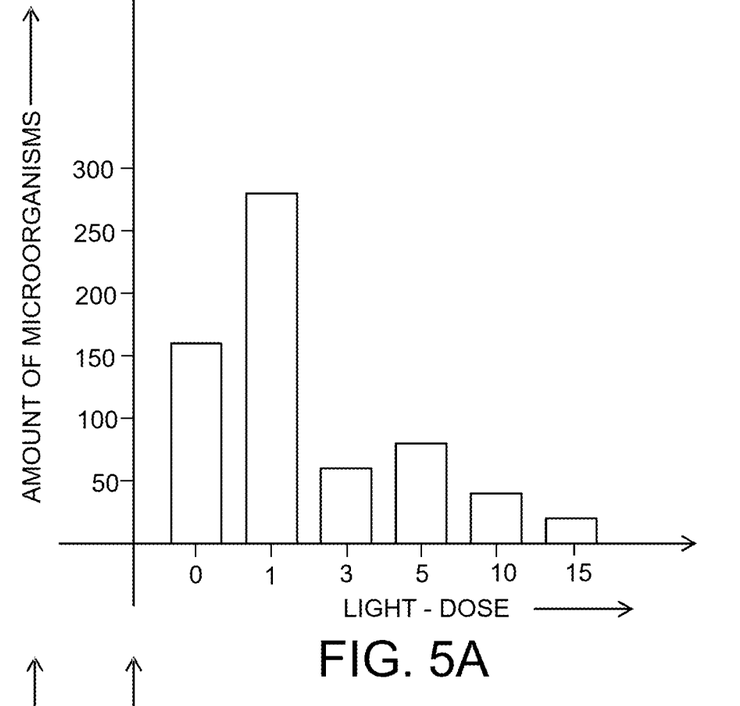
FIG. 5A is a graphical representations of number of microorganisms with respect to light-dose where *Staphylococcus aureus* was illuminated with 405 nm blue light.
Figure 5B:
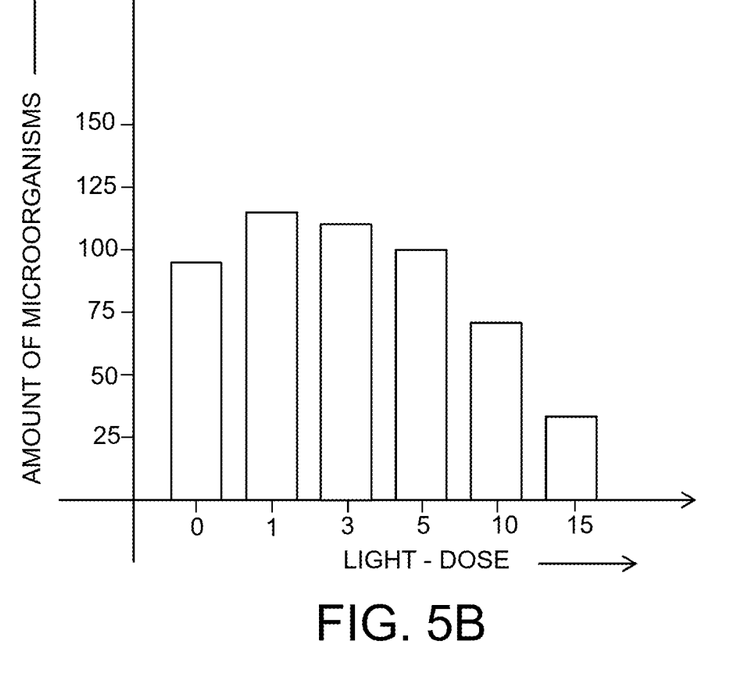
FIG. 5B is a graphical representations of number of microorganisms with respect to light-dose where *Staphylococcus aureus* was illuminated with 470 nm blue light.

Referring to FIGS. 5A and 5B, illustrated are graphical representations of an amount of microorganisms with respect to light-dose (in Ws/cm$^2$), in accordance with different exemplary embodiments of the present disclosure. As shown, the X-axis depicts the light-dose provided by a light assembly and Y-axis depicts amount of microorganisms. As shown in FIG. 5A, a light dose of 1 Ws/cm$^2$ of 405 nm blue light has a stimulatory effect on *Staphylococcus aureus*. Respectively in FIG. 5B a similar stimulatory effect is shown on *Staphylococcus aureus* when exposed to 470 nm blue light exposed to light dose of 1 Ws/cm$^2$. In both cases when the light dose is increased, the amount of microorganisms is reduced.

Referring to FIG. 6, which is a schematic drawing showing the effective area for disinfection. The y-axis is the light intensity (I) measured in W/cm$^2$ and the x-axis is the wavelength (nm) of the light source. FHWM (Full Width Half Maximum) of maximum 25 nm is also shown in the diagram. The area within the two vertical red dotted "bars" (area denoted as A and A' respectively) is represented by the wavelength of light that has been shown to have a biological response. In the case of microbes, these wavelengths are shown to active reaction cascades that as an end-product produces reactive oxygen species inside the microbial cell, which ultimately destroys the microbial cell. The light intensity emitted by the light source outside of the areas A and A' will not have the same effect on microbial cells and are useless in terms of disinfection power or antimicrobial effect. The diagram shows the importance of having a maximum FWHM as narrow as 25 nm, which concentrates the light intensity to the area of biological response in the microbes.

A LED light-source (or other light-source that emits a blue light peak with a wide FWHM will have a lot of energy wasted on wavelengths that do not have a biological effect. The narrower the FWHM is, the less energy is wasted. The target is to have all the blue light emitted only in the areas that are relevant for disinfection.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A system for reducing microorganisms on a surface or in a volume of air, the system comprising:
    a light assembly comprising:
        a first distinct blue light source emitting light having a first peak wavelength of 400-410 nm with a full width half maximum of at most 25 nm, the first peak having a first time averaged intensity $I_1$, selected to target a first photoreactive component of the microorganisms; and
        a second distinct blue light source emitting light having a second peak wavelength of 440-464 nm with a full width half maximum of at most 25 nm, the second peak having a second time averaged intensity $I_2$, selected to target a second photoreactive component of the microorganisms; and
    a processor communicably coupled to the light assembly to control the time averaged intensities of the blue light sources such that the time averaged intensity of first blue light is between 0.67 and 1.33 times the time averaged intensity of the second blue light, wherein the processor is configured to control the light assembly to provide a combined blue light energy dose of more than 1 Ws/cm$^2$ blue light energy at the surface or a cross-section of air.

2. The system according to claim 1, wherein the processor is operable to control the first and second light sources to simultaneously emit the blue lights at the chosen wavelengths.

3. The system according to claim 1, wherein the processor is operable to control the light source to alternatively emit the chosen blue lights at the chosen wavelengths in a periodic manner.

4. The system according to claim 1, further comprising at least one sensor, communicably coupled to the processor, wherein the at least one sensor is operable to detect a presence or movement of an object within a target area subjected to the blue light emitted by the light assembly, and wherein the at least one sensor is operable to instruct the processor to control the time averaged intensities of the blue lights in the target area.

5. The system according to claim 4, wherein the instructing of the processor based on detection of presence or movement of an object comprises switching the light assembly between a disinfecting mode and an ambient mode.

6. The system according to claim 1, wherein the light assembly further comprises a third distinct blue light source having a third peak wavelength of 465-490 nm with a full width half maximum of at most 25 nm, the third peak having a third time averaged intensity $I_3$, to target a third photoreactive component of the microorganisms.

7. The system according to claim 1, further comprising:
at least one light sensor, communicably coupled to the processor, configured to detect the time averaged intensities of the blue lights emitted by the light assembly, wherein the processor is configured to control the time averaged intensities of the blue lights when the blue light energy at the surface exceeds a predefined threshold limit, and
a microbe sensing module, communicably coupled to the processor, configured to detect the presence of microorganisms, wherein the processor is configured to control the time averaged intensities of the blue lights emitted by the light assembly based on the detection of the presence of microorganisms.

8. The system according to claim 1, further comprising a clock module communicably coupled to the processor, wherein the clock module is operable to:
provide a time plan for adjusting the time averaged intensities of the lights emitted by the light assembly to reduce microorganisms;
measure a time duration when the light assembly is arranged to be operated in a disinfecting mode; and
determine a time taken to substantially reduce microorganisms to generate a time-data based on the time plan and the measured time duration.

9. A method for reducing microorganisms on a surface or in a volume of air, using a system comprising a light assembly and a processor, the method comprising:
emitting at least:
a first blue light at a first peak wavelength of 400-410 nm with a full width half maximum of at most 25 nm, the first peak having a first time averaged intensity $I_1$, selected to target a first photoreactive component of the microorganisms; and
a second blue light at a second peak wavelength of 440-464 nm with a full width half maximum of at most 25 nm, the second peak having a second time averaged intensity $I_2$, selected to target a second photoreactive component of the microorganisms;
controlling the time averaged intensities of the blue lights emitted by the light assembly such that the time averaged intensity of the first blue light is between 0.67 and 1.33 times the time averaged intensity of the second blue light; and
controlling the light assembly to provide a combined blue light energy dose of over 1 Ws/cm$^2$ blue light energy at the surface or a cross-section of air of a volume of air for reducing microorganisms.

10. The method according to claim 9, further comprising detecting a presence or movement of an object, using at least one sensor, to instruct the processor to control the time averaged intensities of the blue lights emitted in the target area, wherein instructing the processor based on detection of presence or movement of an object comprises switching the light assembly between a disinfecting mode and an ambient mode.

11. The method according to claim 10, further comprising further emitting a third blue light at a third peak wavelength of 465-490 nm with a full width half maximum of at most 25 nm, the third peak having a third time averaged intensity $I_3$, to target a third photoreactive component of the microorganisms.

12. The method according to claim 9, further comprising:
providing a time plan for adjusting the time averaged intensities of the lights emitted by the light assembly to reduce microorganisms;
measuring a time duration when the light assembly is arranged to be operated in the disinfecting mode; and
determining a time taken to substantially reduce microorganisms to generate a time-data based on the time plan and the measured time duration.

\* \* \* \* \*